United States Patent [19]

Watanabe

[11] Patent Number: 5,000,165

[45] Date of Patent: Mar. 19, 1991

[54] LUMBAR SPINE ROD FIXATION SYSTEM

[76] Inventor: Robert S. Watanabe, 11645 Wilshire Blvd., Ste. 701, Los Angeles, Calif. 90025

[21] Appl. No.: 351,376

[22] Filed: May 15, 1989

[51] Int. Cl.⁵ ............................................. A61F 5/00
[52] U.S. Cl. ......................................... 128/69; 606/61
[58] Field of Search .......................... 128/69; 606/61; 24/230.5 R, 230.5 AD; 248/316.6

[56] References Cited

U.S. PATENT DOCUMENTS

| | | | |
|---|---|---|---|
| 4,269,178 | 5/1981 | Keene | 128/69 |
| 4,274,401 | 6/1981 | Miskew | 128/69 |
| 4,289,123 | 9/1981 | Dunn | 128/84 R |
| 4,361,141 | 11/1982 | Tanner | 128/69 |
| 4,369,769 | 1/1983 | Edwards | 128/69 |
| 4,433,676 | 2/1984 | Bobechko | 606/61 |
| 4,567,884 | 2/1986 | Edwards | 128/69 |
| 4,648,388 | 3/1987 | Steffee | 128/69 |
| 4,653,481 | 3/1987 | Howland | 128/69 |
| 4,854,304 | 8/1989 | Zielke | 128/69 |

FOREIGN PATENT DOCUMENTS 2615095 11/1988 France ............................. 128/69

*Primary Examiner*—V. Millin
*Assistant Examiner*—P. Kubel

[57] ABSTRACT

A lumbar spine fixation system which includes two spaced lumbar rods extending upwardly from the sacrum on each side of the lumbar spine. The upper ends of the lumbar rods are affixed to the spine by the use of pedicle screws. In the practice of the present invention, fixation of the lower ends of the rods is achieved by mounting an offset hook onto the lower end of each rod. The hook is configured to extend to the alar portion of the sacrum which is laterally placed from the sacral facet. The offset sacral hooks allow for the placement of the rods toward the midline and protect the laminar area of the spine which is frequently removed in a laminectomy. The sacral hooks can be further stabilized with a screw which goes from the sacral hook out laterally into the thick portion of the sacrum. This provides for further compression fixation of the sacral hook. A gear nut system is provided to facilitate the fixation of the screw holder and sacral hook.

7 Claims, 3 Drawing Sheets

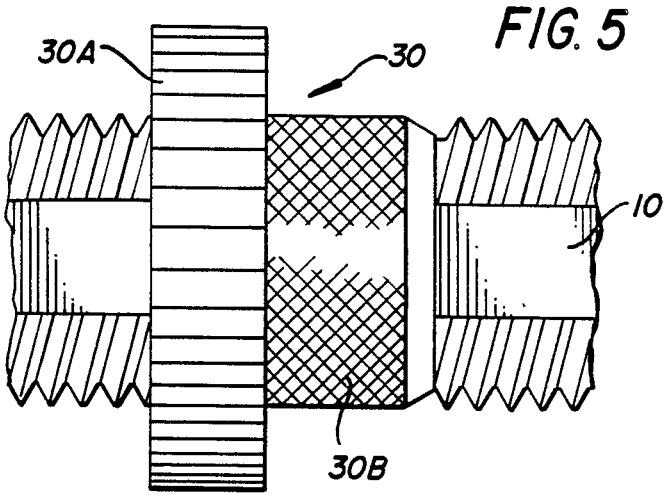
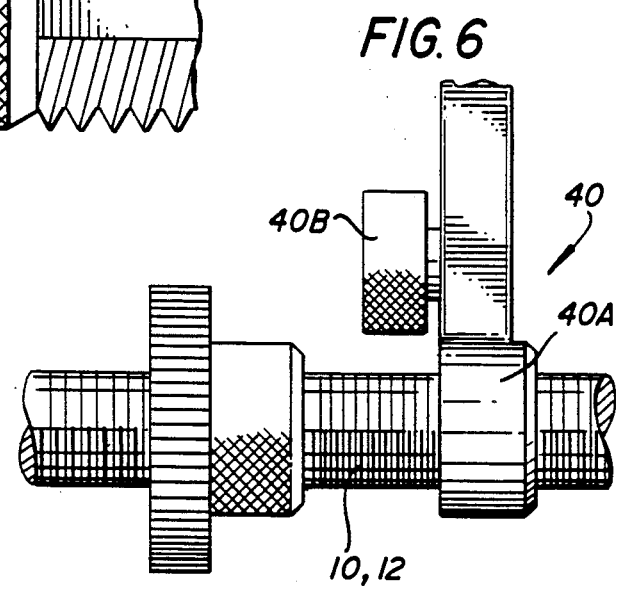
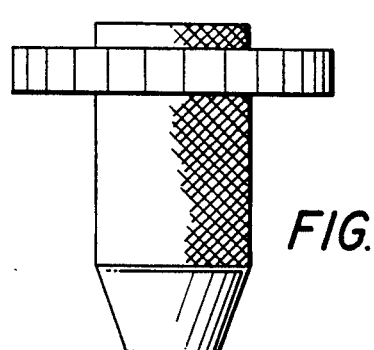
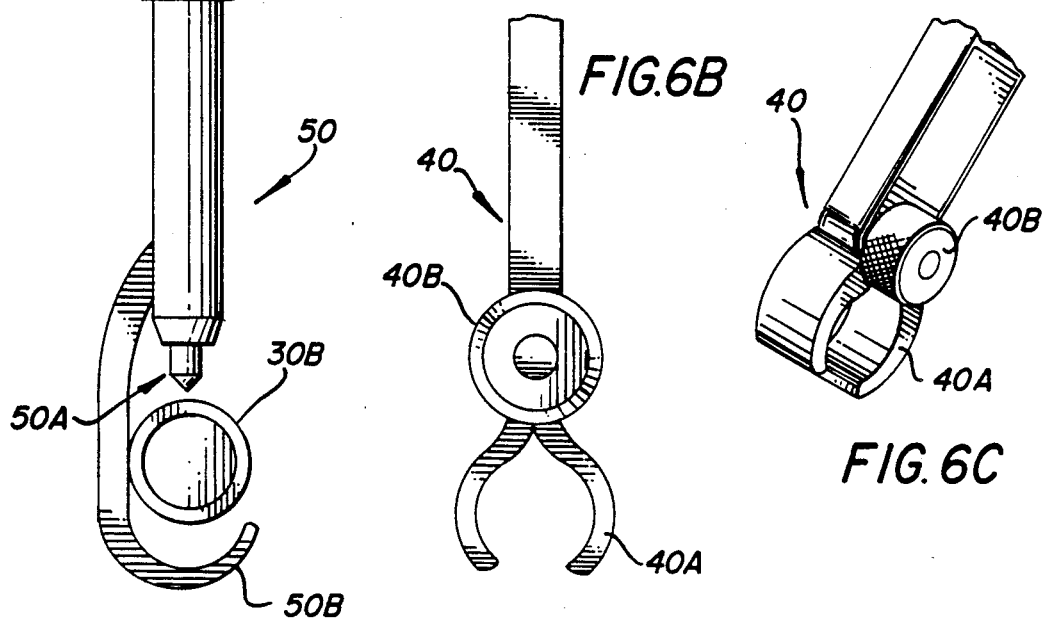

LUMBAR SPINE ROD FIXATION SYSTEM

BACKGROUND OF THE INVENTION

The invention is concerned with a lumbar spine fixation system which is particularly intended for the stabilization of an unstable lower back. Instability of the lower back is brought about by congenital anomalies, multiple surgeries, or trauma. Such instability usually results in the patient being totally incapacitated due to continuous pain.

As pointed out in U.S. Pat. No. 4,653,481, various types of spinal column disorders are known, such as scoliosis, kyphosis, spondylolesthesis, and other problems such as ruptured or slipped discs, broken or fractured spinal column, and the like. Various forms of instrumentation and procedures are known for the surgical treatment of spinal disorders, for example, Harrington Spiral Instrumentation, Bobechko Hooks, Edwards Hooks and Rod Sleeves, Luque Segmental Spinal Instrumentation and Luque Rectangles, the Dunn Anterior Spinal System, and the Kostuiq-Harrington Instrumentation, to mention only a few. These and other systems are described in one or more of the following U.S. Pat. Nos. 4,433,676; 4,369,769; 4,269,178; 4,409,968; and 4,289,123.

Some of the systems referred to above utilize hook-type members which are merely hooked over the laminae or on selected transverse processes of the spine. Other systems, such as the Luque Segmental Spinal Rectangles, used to stabilize spinal fractures and low back fusions, use wires to secure a rectangle to the spine. In some of the prior art systems, screws are used to hold a rod in place. In other systems, screws are used to hold a slotted plate in place, the location of the screws and slots being such that the plate is moved in order to align the plate apertures or slots with the end of the screw, a nut being used to hold the plate to the screw. The latter arrangement is sometimes referred to as Steppee Plate.

Attempts have been made in the past to use the Harrington Spinal Rod System for lumbar spine fixation. However, the Harrington System is intended primarily for the treatment of scoliosis, and the Harrington hooks do not always hold properly when used for lumbar spine fixation. In lumbar spine fixation using the Harrington System, the hooks must be placed in the laminae portion of the spine and can be unstable and/or cause injury to the spinal cord.

Luque was one of the pioneers, in the field of pedicular fixation. He advocated the use of pedicle screws and sublaminal wires for the fixation of the spine. The fixation system of the present invention uses two lumbar rods placed on each side of the spine adjacent to the lumbar vertebrae. The upper ends of the rods are affixed by the pedicle screws to the pedicle of the lumbar vertebrae. However, especially designed sacral hooks are used to affix the lower ends of the rods to the alar portion of the sacrum because pedicle screws alone are inadequate for sacral fixations.

The sacral hooks have an offset design to enable them to hook, which hooks to the alar portion of the sacrum. The alar portion lies in an area away from the cauda equina nerve roots and is a relatively safe area. The bone in the alar portion is relatively thick and will provide for excellent fixation of the sacral hook. Sacral screws are also inserted to fix the hook sacral hooks to the sacrum to provide further copression fixation.

The offset sacral hooks allow the lumbar rod to be placed medially over the area of the laminectomy and protect the cord. It also allows for the placement of the bone graft just lateral to the rods and in the area over the facets. The above configuration allows for a minimal dissection of the lumbar spine during surgery with a consequent decrease in the surgical time and blood loss.

BRIEF DESCRIPTION OF THE DRAWINGS

FIG. 5 is a specially designed gear nut which replaces the hexagonal nut which is commonly used in the lumbar fixation systems;

FIG. 6A is a side view of a gear nut spinner which enables the rapid adjustment of the gear nut of FIG. 5;

FIG. 6B is a side view of the spinner turned 90° from the view of FIG. 6A;

FIG. 6C is a perspective view of the spinner; and

FIG. 7 is a gear nut crimp which serves deform a portion of the gear nut 59 prevent it from getting loose.

DETAILED DESCRIPTION OF THE ILLUSTRATED EMBODIMENT

Figure 1:
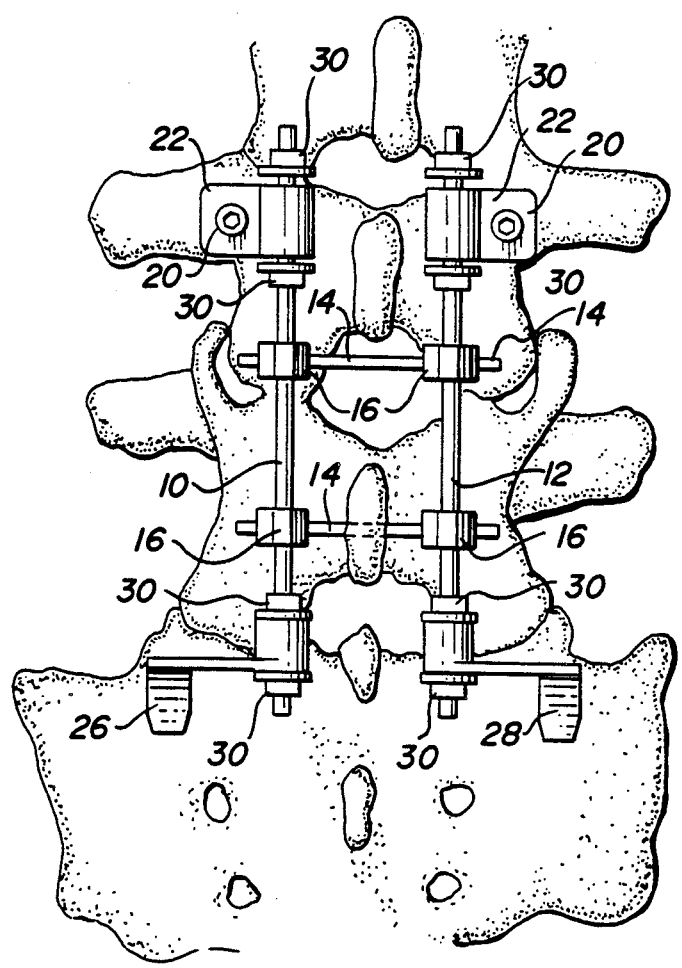
FIG. 1 is a rear view of one embodiment of the lumbar fixation system of the present invention in place adjacent to the lumbar spine.
Figure 2:
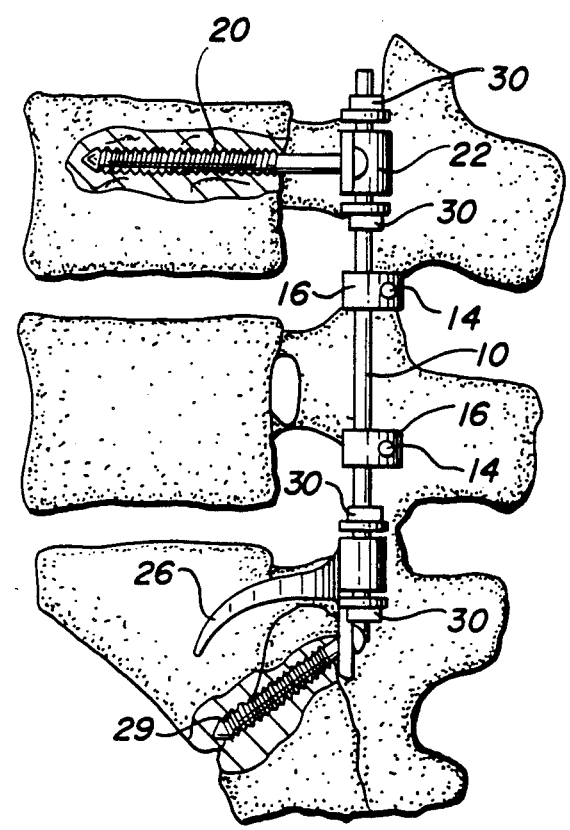
FIG. 2 is a side view of the system of FIG. 1 taken to the left of FIG. 1.

The fixation system of the invention, as shown in FIGS. 1 and 2, includes first and second lumbar rods 10, 12 which are positioned on either side of the lumbar spine. The lumbar rods 10, 12 are held in spaced and parallel relationship by transverse connector rods 14 which are coupled to rods 10 and 12 by couplers 16. Couplers 16 are adjustable along the lumbar rods to permit the spacing between rods 10 and 12 to be adjusted, as well as the location of connector rods 14 along the rods 10 and 12. Connector rods 14 provide cross-stabilization for rods 10 and 12.

The upper ends of the rods 10 and 12 are affixed to the pedicle of the lumbar vertebrae by pedicle screws, such as screw 20 in FIG. 2. Screws 20 are coupled to rods 10 and 12 by couplers 22. Couplers 22 may be adjustably set along rods 10 and 12.

Figure 3A:
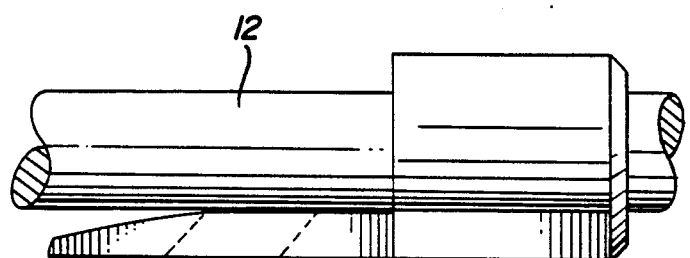
FIG. 3A is a side view of a hook member which is used in the system of FIGS. 1 and 2.
Figure 3B:
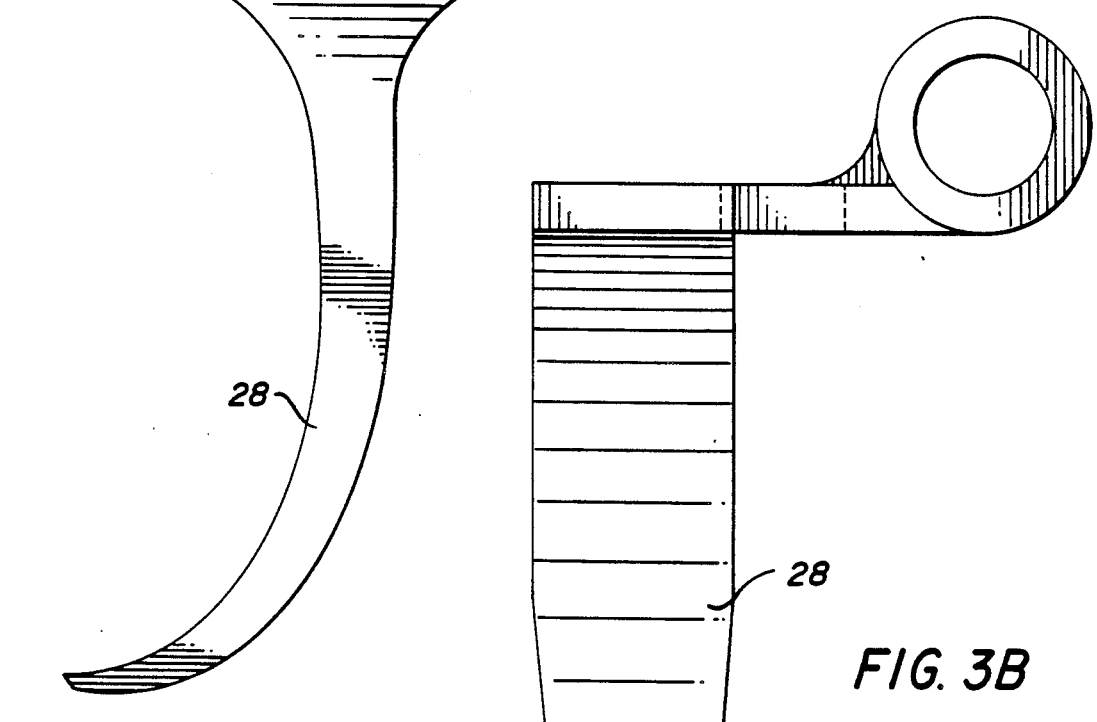
FIG. 3B is a front view of the hook of FIG. 3A.
Figure 4:
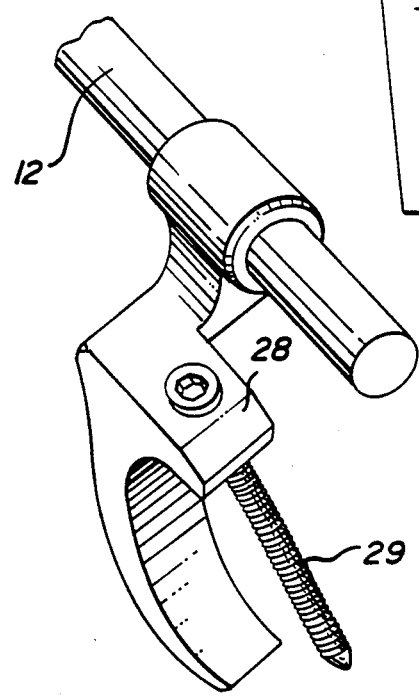
FIG. 4 is a perspective representation of the hook of FIGS. 3A and 3B.

The lower ends of the rods 10 and 12 are affixed by of said sacral hooks 26, 28. The hooks are coupled to the rods and are adjustable along the rods. The hooks attach the lower ends of the rods 10, 12 to the sacrum. For this purpose, the hooks extend into the alar portion of the sacrum. Sacral screws, such as screw 29, may be used, in addition to hooks 26, 28 if so desired. Details of hook 28 are shown in FIGS. 3A, 3B and 4. Hook 26 may be a mirror image of hook 28.

A number of gear nuts 30 are used for mounting the couplers 22 and hooks 26, 28 to the rods 10 and 12. The gear nuts are threaded to the rods, and they enable rapid adjustments and fixations of the couplers 22 and hooks 26, 28 with respect to the rods 10 and 12.

As shown in FIG. 5, each gear nut has a large diameter end equipped with radial gear teeth, and a reduced diameter knurled end 30B.

In the narrow confines of the lumbar spine, the hex nut used in the prior art systems can be turned with the wrench only ¼ rotation at a time and is extremely time consuming. The gear nut 30 allows for the rapid rotation and adjustment of the components. The reduced diameter end 30B can be crimped onto the rod to prevent the loosening which commonly occurs when the hex nut is used.

The use of the gear nut 30 of FIG. 5 allows for the rapid adjustment and fixation of the screw holders 22 and the sacral hooks 26. The commonly used hex nut is extremely difficult to adjust in the narrow confines of the lumbar spine.

A motorized drive 40 may be used in conjunction with the gear nuts 30 which greatly factiliates the adjustment and palcement of the rods and hooks. Such a drive unit is shown in FIGS. 6A, 6B, 6C.

A gear nut crimping tool 50 (FIG. 7) may be used to crimp the end 30B of the gear nut against the lumbar rod 10 or 12 and prevent the loosening and migration of the nut 30. This has been a common problem in the lumbar fixation systems and is obviated by the crimp.

The large diameter end 30A of the gear nut of FIG. 5 may be spun by hand, or by a suitable instrument, for rapid adjustment of the system. The knurled reduced diameter end 30B of the gear nut may be driven by a mechanized spinner 40 of FIGS. 6A, 6B, 6C. The reduced diameter end 30B is also intended to receive the jaws 50A of the crimping tool 50 of FIG. 7.

The jaws 40A of the spinner 40 of FIGS. 6A, 6B, 6C may be opened and closed in a plier-like action to grasp the lumbar rod 10 or 12, with a wheel 40B engaging the reduced diameter end 30B of gear nut 30.

The spinner may be coupled to a micro drill which drives wheel 40B and gear nut 30 for rapid adjustment of the system.

The gear nut crimping unit 50 of FIG. 7 may be used safely to crush the reduced diameter end 30B of the gear nut against the surface of rod 10 or 12. This crimping action serves to prevent loosening and resulting migration of the nut.

The crimping unit is designed to permit crimping of the gear nut in a confined space. The unit is provided with a hook 50B which effectively stabilizes the lumbar rod during the crimping action and prevents accidental dislodgement.

The invention provides, therefore, a lumbar fixation system which is intended primarily for the stabilization of the lumbar spine. As shown and described, the sacrum is stabilized by special sacral hooks 26 and 28 which extend into the alar portion of the sacrum. The upper segments of the lumbar spine, on the other hand, are stabilized by the use of pedicular screws 20.

The rod fixation system of the invention is utilized for the salvage of a failed back, spondylolisthes, fractures, and other instability problems. The rods 10 and 12 are relatively compact because short distances are involved, for example, these distances are in the range of 6–15 centimeters. There is very little stress on the rods since most of the force is in the longitudinal plane.

The system of the invention is predicated on the fact that affixation to the lumbar vertebrae by pedicle screws is excellent, but affixation to the sacrum by pedicle screws is totally inadequate. The stress upon the pedicle screws is at a perpendicular plane and if the fusion does not occur there will be a loosening of the screws. There is also a danger in this area because of the proximity of the cauda equina which can be damaged with the screws.

The system of the present invention, as described above, includes the insertion of a hook into the alar portion of the sacrum just lateral to the sacral facet where there is a large area of bone available for fixation. The hook is configured to exert a vertical force into the sacral alar and provide for excellent fixation. The sacral hook screw is inserted for further compression stabilization when necessary. The offset configuration of the sacral hook allows it to be placed into a safe region of the sacrum away from the cauda equina and underlying vascular structures in front of the sacrum.

The system of the invention may be designed so that screws 20 may be inserted into the pedicle at an angle. Moreover, canulated screws may be used, and guide wires may be placed in the pedicle and utilized for the fixation so as to lessen the likelihood of injury to the nerve roots and cauda.

The sacral hooks 26 and 28 are inserted into the sacrum with a minimum of lateral dissection. The lumbar musculature remain attached to the sacrum and by slipping the hooks beneath the muscles, there is less chance for the hooks to be displaced. A screw is placed into the sacral hook and sacrum to provide further fixation.

The stabilization of the screw holder and sacral hook is facilitated by the specially designed gear nut. All of the present spinal rod systems use a standard hexagonal nut which is extremely difficult to adjust in the back. This is due to the depth of the incision and the difficulty in rotating the nut with a hex wrench. The gear nut will reduce the surgical time due to the motorized gear nut driver and wrench. When the gear nut is in position, it is tightened with the gear nut wrench and held in place with the special crimping tool.

It will be appreciated that while a particular embodiment of the invention has been shown and described, modifications may be made. It is intended in the claims to cover all modifications which come within the spirit and scope of the invention.

I claim:

1. A support fixation system for the lumbar spine comprising: first and second lumbar rods to be placed adjacent to the lumbar spine on each side thereof to form a rigid support structure therefor; first and second pedicle screws to be threaded into the pedicle of the lumbar vertebrae; first and second couplers adjustable along said rods for mounting said sacral screws to the upper ends of respective ones of said rods; first and second off-set sacral hooks; and third and fourth couplers adjustable along said rods for mounting said hooks to the lower ends of respective ones of said lumbar rods, said offset sacral hooks being configured to extend laterally to the longitudinal axes of the rods away from the lumbar spine and into the alar portion of the sacram.

2. The support fixation system defined in claim 1, and which includes at least one transverse stabilizing interconnecting rod attached to each of said lumbar rods and extending therebetween to maintain said lumbar rods in spaced and parallel relationship.

3. The support fixation system defined in claim 1, and which includes first and second sacral screws mounted on the lower ends of respective ones of said rods and positioned to enter the sacrum and provide stabilization for the support fixation system.

4. The support fixation system defined in claim 1, in which at least one of said couplers includes a nut threaded to the corresponding lumbar rod.

5. The support fixation system defined in claim 4, in which said nut has a large diameter end to permit rapid manual rotation and a reduced diameter end for receiving a crimping unit and/or a mechanized rotating unit.

6. The support fixation system defined in claim 5, in which said large diameter end has radial teeth extending around the perimeter thereof.

7. The support fixation system defined in claim 5, in which said reduced diameter end has a knurled configuration.

* * * * *